United States Patent
Yanagawa et al.

(10) Patent No.: US 9,776,934 B2
(45) Date of Patent: Oct. 3, 2017

(54) METHOD FOR PRODUCING MONOCYCLIC AROMATIC HYDROCARBONS

(75) Inventors: Shinichiro Yanagawa, Tokyo (JP); Masahide Kobayashi, Tokyo (JP); Ryoji Ida, Tokyo (JP); Yasuyuki Iwasa, Tokyo (JP)

(73) Assignee: JX Nippon Oil Energy Corporation, Tokyo (JP)

( * ) Notice: Subject to any disclaimer, the term of this patent is extended or adjusted under 35 U.S.C. 154(b) by 348 days.

(21) Appl. No.: 14/006,778

(22) PCT Filed: Mar. 23, 2012

(86) PCT No.: PCT/JP2012/057489
§ 371 (c)(1),
(2), (4) Date: Sep. 23, 2013

(87) PCT Pub. No.: WO2012/133170
PCT Pub. Date: Oct. 4, 2012

(65) Prior Publication Data
US 2014/0012055 A1 Jan. 9, 2014

(30) Foreign Application Priority Data
Mar. 25, 2011 (JP) .................. 2011-067878

(51) Int. Cl.
*C07C 4/06* (2006.01)
*C10G 45/64* (2006.01)
*C10G 63/04* (2006.01)
*C10G 35/06* (2006.01)

(52) U.S. Cl.
CPC .............. *C07C 4/06* (2013.01); *C10G 35/065* (2013.01); *C10G 45/64* (2013.01); *C10G 63/04* (2013.01); *C10G 2300/1033* (2013.01); *C10G 2300/301* (2013.01); *C10G 2400/30* (2013.01)

(58) Field of Classification Search
CPC ...... C10G 35/065; C10G 63/04; C10G 45/64; C07C 4/06
See application file for complete search history.

(56) References Cited

U.S. PATENT DOCUMENTS

| 4,585,545 A | 4/1986 | Yancey, Jr. et al. |
| 2009/0314683 A1 | 12/2009 | Matsushita |
| 2011/0083999 A1* | 4/2011 | Simon .................. B01J 29/064 208/88 |

FOREIGN PATENT DOCUMENTS

| EP | 0038140 A1 | 10/1981 |
| EP | 0212788 A1 | 3/1987 |
| GB | 1287722 A | 9/1972 |
| JP | S56-157488 A | 12/1981 |
| JP | S61-148295 A | 7/1986 |
| JP | S61-283687 A | 12/1986 |
| JP | H03-002128 A | 1/1991 |
| JP | H03-026791 A | 2/1991 |
| JP | H03-052993 A | 3/1991 |
| JP | 2007-154151 A | 6/2007 |
| JP | 2009-235248 A | 10/2009 |
| WO | 2010061986 A1 | 6/2010 |
| WO | 2010109897 A1 | 9/2010 |
| WO | 2011013272 A1 | 2/2011 |

OTHER PUBLICATIONS

Extended European Search Report issued Nov. 6, 2014 in EP Application No. 12762798.2.
Int'l Search Report issued May 29, 2012 in Int'l Application No. PCT/JP2012/057489.
Office Action issued Jul. 10, 2014 in CN Application No. 201280014586.6.
Notice of Allowance issued Dec. 15, 2015 in JP Application No. 2011067878.

* cited by examiner

*Primary Examiner* — Jason Chong
(74) *Attorney, Agent, or Firm* — Panitch Schwarze Belisario & Nadel LLP

(57) ABSTRACT

A method of producing monocyclic aromatic hydrocarbons includes bringing a light feedstock oil having a 10 vol % distillation temperature of 140° C. to 205° C. and a 90 vol % distillation temperature of 300° C. or lower, which has been prepared from a feedstock oil having a 10 vol % distillation temperature of 140° C. or higher and a 90 vol % distillation temperature of 380° C. or lower, into contact with a catalyst for monocyclic aromatic hydrocarbon production containing a crystalline aluminosilicate, in which a content ratio of monocyclic naphthenobenzenes in the light feedstock oil is adjusted by distillation of the feedstock oil such that the content ratio of monocyclic naphthenobenzenes in the light feedstock oil is higher than a content ratio of monocyclic naphthenobenzenes in the feedstock oil.

7 Claims, No Drawings

US 9,776,934 B2

METHOD FOR PRODUCING MONOCYCLIC AROMATIC HYDROCARBONS

CROSS-REFERENCE TO RELATED APPLICATION

This application is a Section 371 of International Application No. PCT/JP2012/057489, filed Mar. 23, 2012, which was published in the Japanese language on Oct. 4, 2012, under International Publication No. WO 2012/133170 A1, and the disclosure of which is incorporated herein by reference.

TECHNICAL FIELD

The present invention relates to a method of producing monocyclic aromatic hydrocarons.

Priority is claimed on Japanese Patent Application No. 2011-067878, filed Mar. 25, 2011, the content of which is incorporated herein by reference.

BACKGROUND ART

In recent years, techniques have been sought that can efficiently produce monocyclic aromatic hydrocarbons having 6 to 8 carbon atoms (such as benzene, toluene, ethylbenzene and xylene, hereinafter, which are collectively referred to as a "BTX fraction" or "BTX"), which can be used as high-octane gasoline base stocks or petrochemical feedstocks and offer high added value, from feedstocks containing a polycyclic aromatic fraction such as a light cycle oil (hereinafter, also referred to as "LCO"), which is a cracked light oil produced by a fluid catalytic cracking (hereinafter, also referred to as "FCC") apparatus, and has been mainly used as light oil or heavy oil fraction.

Examples of known methods for producing a BTX fraction from a polycyclic aromatic fraction include the following methods.

(1) Methods of hydrocracking hydrocarbons containing a polycyclic aromatic fraction in a single stage (see Patent Literatures 1 and 2).

(2) Methods of subjecting hydrocarbons containing a polycyclic aromatic fraction to a hydrotreatment in a preliminary stage and then hydrocracking in a subsequent stage (see Patent Literatures 3 to 5).

(3) A method of converting hydrocarbons containing a polycyclic aromatic fraction directly into a BTX fraction using a zeolite catalyst (see Patent Literature 6).

(4) Methods of converting a mixture of hydrocarbons containing a polycyclic aromatic fraction and light hydrocarbons having 2 to 8 carbon atoms into a BTX fraction using a zeolite catalyst (see Patent Literatures 7 and 8).

However, the methods of (1) and (2) require the addition of high-pressure molecular hydrogen, and there is a problem of a high level of hydrogen consumption. Further, under the hydrogenation conditions, an unnecessary LPG fraction is by-produced in a large amount during production of the target BTX fraction, and not only is energy required to separate the LPG fraction, but also the feedstock efficiency deteriorates.

The method of (3) is not sufficient in terms of conversion of the polycyclic aromatic fraction.

The methods of (4) is designed to improve the thermal balance by combining a production technique for BTX which uses light hydrocarbons as a feedstock and a production technique for BTX which uses hydrocarbons containing a polycyclic aromatic fraction as a feedstock, but is not designed to improve the yield of BTX from the polycyclic aromatic fraction.

CITATION LIST

Patent Literature

[Patent Literature 1] Japanese Unexamined Patent Application, First Publication No. S61-283687
[Patent Literature 2] Japanese Unexamined Patent Application, First Publication No. S56-157488
[Patent Literature 3] Japanese Unexamined Patent Application, First Publication No. S61-148295
[Patent Literature 4] UK Patent No. 1,287,722
[Patent Literature 5] Japanese Unexamined Patent Application, First Publication No. 2007-154151
[Patent Literature 6] Japanese Unexamined Patent Application, First Publication No. H3-2128
[Patent Literature 7] Japanese Unexamined Patent Application, First Publication No. H3-52993
[Patent Literature 8] Japanese Unexamined Patent Application, First Publication No. H3-26791

SUMMARY OF INVENTION

Technical Problem

An object of the present invention is to provide a method of producing Monocyclic aromatic hydrocarbons.

Monocyclic aromatic hydrocarbons can be produced by a cracking and ring-opening reaction of naphthenobenzenes contained in a feedstock oil. On the other hand, polycyclic aromatic hydrocarbons can be produced by the dehydrogenation reaction of naphthenobenzenes contained in a feedstock oil, and the catalyst activity is decreased by coking the generated polycyclic aromatic hydrocarbons deposited on a catalyst.

Therefore, to increase of the ratio of the naphthenobenzenes is not always lead to increase the yield of the monocyclic aromatic hydrocarbons.

Further, when a simple condition for suppressing only dehydrogenation capacity was applied, the cyclization and dehydrogenation of saturated hydrocarbon, which simultaneously proceeded, were suppressed, and therefore, the yield of monocyclic aromatic hydrocarbons could not be increased.

As a result of intensive research, the present inventors found out that monocyclic aromatic hydrocarbons could be efficiently produced by using a lightened feedstock oil (light feedstock oil) which had been lightened by distilling a feedstock oil to include a large amount of monocyclic naphthenobenzenes among naphthenobenzenes, and by selecting proper catalysts and reaction conditions, thereby completing the present invention.

Solution to Problem

[1] A method of producing monocyclic aromatic hydrocarbons including bringing a light feedstock oil having a 10 vol % distillation temperature of 140° C. to 205° C. and a 90 vol % distillation temperature of 300° C. or lower, which has been prepared from a feedstock oil having a 10 vol % distillation temperature of 140° C. or higher and a 90 vol % distillation temperature of 380° C. or lower, into contact with a catalyst for monocyclic aromatic hydrocarbon production containing a crystalline aluminosilicate, in which a content ratio of monocyclic naphthenobenzenes in the light feedstock oil is adjusted by distillation of the feedstock oil such that the content ratio of monocyclic naphthenobenzenes in the light feedstock oil is higher than a content ratio of monocyclic naphthenobenzenes in the feedstock oil.

[2] The method of producing monocyclic aromatic hydrocarbons according to [1], in which the content ratio of monocyclic naphthenobenzenes in the light feedstock oil is 10 mass % to 70 mass %.

[3] The method of producing monocyclic aromatic hydrocarbons according to [1] or [2], wherein the content ratio of monocyclic naphthenobenzenes in the light feedstock oil is 12 mass % to 70 mass %.

[4] The method of producing monocyclic aromatic hydrocarbons according to any one of [1] to [3], wherein the feedstock oil contains a light cycle oil which is produced by a fluid catalytic cracking apparatus.

Advantageous Effects of Invention

According to the method of producing monocyclic aromatic hydrocarbons of the present invention, it is possible to produce monocyclic aromatic hydrocarbons having 6 to 8 carbon atoms from a feedstock oil containing polycyclic aromatic hydrocarbons with high yield.

DESCRIPTION OF EMBODIMENTS

A method of producing monocyclic aromatic hydrocarbons according to the present invention includes bringing a light feedstock oil having a 10 vol % distillation temperature of 140° C. to 205° C. and a 90 vol % distillation temperature of 300° C. or lower, which has been prepared from a feedstock oil having a 10 vol % distillation temperature of 140° C. or higher and a 90 vol % distillation temperature of 380° C. or lower, into contact with a catalyst containing a crystalline aluminosilicate, in which a content ratio of monocyclic naphthenobenzenes in the light feedstock oil is adjusted by distillation of the feedstock oil such that the content ratio of monocyclic naphthenobenzenes in the light feedstock oil is higher than a content ratio of monocyclic naphthenobenzenes in the feedstock oil.

In the method of producing monocyclic aromatic hydrocarbons according to the present invention, a feedstock oil is distilled to obtain a light feedstock oil in which a content ratio of monocyclic naphthenobenzenes is increased, the light feedstock oil is brought into contact with a catalyst for monocyclic aromatic hydrocarbon production containing a crystalline aluminosilicate, polycyclic aromatic hydrocarbons are partially hydrogenated by a hydrogen transfer reaction from saturated hydrocarbons using the saturated hydrocarbons contained in the light feedstock oil as a hydrogen donating source, and the polycyclic aromatic hydrocarbons are converted to monocyclic aromatic hydrocarbons by ring-opening. Furthermore, conversion to monocyclic aromatic hydrocarbons can also be achieved by cyclizing and dehydrogenating saturated hydrocarbons obtainable from the light feedstock oil or in a cracking process. Also, monocyclic aromatic hydrocarbons having 6 to 8 carbon atoms can also be obtained by cracking monocyclic aromatic hydrocarbons having 9 or more carbon atoms. A product containing monocyclic aromatic hydrocarbons is obtained by the complex process of the reaction. Thereby, a product containing monocyclic aromatic hydrocarbons having 6 to 8 carbon atoms and a heavy fraction having 9 or more carbon atoms can be obtained.

This product includes, hydrogen, methane, ethane, ethylene, LPG (propane, propylene, butane, butene and the like), and the like, in addition to the monocyclic aromatic hydrocarbons and the heavy fraction. Furthermore, the heavy fraction includes large amounts of bicyclic aromatic hydrocarbons such as naphthalene, methylnaphthalene, and dimethylnaphthalene, and also includes tricyclic or higher-cyclic aromatic hydrocarbons such as anthracene depending on feedstock oils. In the specification, these bicyclic aromatic hydrocarbons and tricyclic or higher-cyclic aromatic hydrocarbons are collectively described as polycyclic aromatic hydrocarbons.

(Feedstock Oil)

The feedstock oil used in the present invention is an oil having a 10 vol % distillation temperature of 140° C. or higher and a 90 vol % distillation temperature of 380° C. or lower. When an oil having a 10 vol % distillation temperature of lower than 140° C. is used, monocyclic aromatic hydrocarbons are produced by light oil fraction, and therefore, the oil is not suitable for the gist of the present invention. Furthermore, when an oil having a 90 vol % distillation temperature of higher than 380° C. is used, not only the yield of monocyclic aromatic hydrocarbons decreases, but also the amount of coke deposition on the catalyst for monocyclic aromatic hydrocarbon production increases, and the catalytic activity tends to rapidly decrease.

The lower limit of the 10 vol % distillation temperature of the feedstock oil is 140° C. or higher and preferably 150° C. or higher, and the upper limit is preferably 300° C. or lower. In addition, the upper limit of the 90 vol % distillation temperature of the feedstock oil is 380° C. or lower, and preferably 360° C. or lower, and the lower limit is preferably 180° C. or higher.

Examples of the feedstock oil having a 10 vol % distillation temperature of 140° C. or higher and a 90 vol % distillation temperature of 380° C. or lower include a light cycle oil (LCO) produced by a fluid catalytic cracking (FCC) apparatus, coal liquefied oil, straight run kerosene, straight run light oil, coker kerosene, coker light oil and the like.

Here, the term polycyclic aromatic fraction as used herein means the total value of the content of bicyclic aromatic hydrocarbons (bicyclic aromatic fraction) and the content of tricyclic or higher-cyclic aromatic hydrocarbons (tricyclic or higher-cyclic aromatic fraction), which is measured according to JPI-5S-49 "Petroleum Products—Determination of Hydrocarbon Types—High Performance Liquid Chromatography", or analyzed by an FID gas chromatographic method or a two-dimensional gas chromatographic method.

Hereinbelow, when the contents of polycyclic aromatic hydrocarbons, bicyclic aromatic hydrocarbons, and tricyclic or higher-cyclic aromatic hydrocarbons are expressed in vol %, the content has been measured according to JPI-5S-49, while when the content is expressed in mass %, the content has been measured based on an FID gas chromatographic method or a two-dimensional gas chromatographic method.

The content ratio of components other than polycyclic aromatic fraction (such as monocyclic aromatic fraction, paraffin fraction (excepting naphthene fraction), and olefin fraction) in the feedstock oil is not particularly limited. Further, within the range of not remarkably inhibiting the targeted reaction, the feedstock oil may contain hetero atoms such as sulfur, oxygen, nitrogen and the like.

In the feedstock oil, the content ratio of monocyclic naphthenobenzenes is preferably 5 to 60 mass %, and more preferably 6 to 55 mass %, with respect to 100 mass % of the feedstock oil.

Further, the value represented by [the content ratio of monocyclic naphthenobenzenes in the light feedstock oil]/[the content ratio of monocyclic naphthenobenzenes in the feedstock oil] is preferably 1.1 to 10, and more preferably 1.2 to 9.

(Light Feedstock Oil)

The light feedstock oil used in the present invention is oil having a 10 vol % distillation temperature of 140 to 205° C. and a 90 vol % distillation temperature of 300° C. or lower, which can be obtained by distillation of the aforementioned feedstock oil to cut (i.e., to separate a low-boiling fraction from a high-boiling fraction) so as to lighten the feedstock oil. In the case of the oil having a 10 vol % distillation temperature of lower than 140° C., monocytic aromatic hydrocarbons must be produced by a very light hydrocarbon oil, and therefore, the oil is not suitable for the gist of the present invention. On the other hand, since the boiling point of indane is 177° C. and the boiling point of tetralin is 206° C., which are classified into monocyclic naphthenobenzenes, the upper limit of the 10 vol % distillation temperature is 205° C. or lower, preferably 180° C. or lower, and more preferably 170° C. or lower, in terms of improving the content ratio of monocyclic naphthenobenzenes in the light feedstock oil so as to produce BTX effectively. Further, when the upper limit of the 90 vol % distillation temperature is more than 300° C., the amount of the monocyclic naphthenobenzenes capable of producing BTX effectively is greatly decreased, and the amount of tricyclic or higher-cyclic aromatic hydrocarbons which cause coke deposition on the catalyst is increased, which is not preferable. Moreover, since the boiling point of the bicyclic naphthenobenzenes such as dihydrophenanthrene and tetrahydroanthracene is more than 300° C., the cracking of the aromatic ring portion thereof hardly proceeds, and therefore, the yield of monocyclic aromatic hydrocarbons cannot be improved. Therefore, the large amount of bicyclic naphthenobenzenes is not always preferred, and the upper limit of the 90 vol % distillation temperature is 300° C. or lower. There is a case where the large amount of monocyclic naphthenobenzenes having a short alkyl chain is included depending on feedstock oils, the 90 vol % distillation temperature is preferably 280° C. or lower, and more preferably 270° C. or lower. On the other hand, the lower limit of the 90 vol % distillation temperature is not particularly limited, and in terms of increasing the content ratio of monocyclic naphthenobenzenes, the lower limit is preferably 180° C. or higher, more preferably 220° C. or higher, and still more preferably 230° C. or higher.

By adjusting the distillation range of light feedstock oil to a predetermined range by changing the cut point of distillation, the content ratio of monocyclic naphthenobenzenes in the light feedstock oil can be higher than the content ratio of the monocyclic naphthenobenzenes in the feedstock oil. As the method of distilling the feedstock oil, a method of distilling the feedstock oil using a conventional distillation apparatus can be mentioned, and the cut point is appropriately adjusted to obtain a light feedstock oil having a predetermined distillation range. As an example of the distillation apparatus, an apparatus capable of distillation and separation of a plurality of fractions by using a multi-stage distillation apparatus such as a stripper can be mentioned. Here, the light feedstock oil may be either oil which has been subjected to fractional distillation in advance to adjust the distillation range to the predetermined range by using a distillation apparatus attached to the apparatus for producing feedstock oil (e.g., fluid catalytic cracking apparatus), or oil obtained by distillation of feedstock oil so as to adjust the distillation range to the predetermined range by using a separately located distillation apparatus. Here, the 10 vol % distillation temperature and 90 vol % distillation temperature as used herein mean values measured according to JIS K2254 "Petroleum products-Determination of distillation characteristics".

In addition, in the light feedstock oil, the content ratio of monocyclic naphthenobenzenes is preferably adjusted to 10 mass % to 70 mass % with respect to 100 mass % of the light feedstock oil, and more preferably 12 mass % to 70 mass %. The upper level of the content ratio of monocyclic naphthenobenzenes is not particularly limited, and it is difficult to prepare the light feedstock oil having a content ratio of monocyclic naphthenobenzenes of more than 70 mass % by the aforementioned methods. The term monocyclic naphthenobenzene as used herein means, for example, a compound in which a monocyclic aromatic ring and a naphthene ring coexist in one molecule as in a tetralin skeleton.

Specifically, tetralins, indanes, octahydrophenanthrenes, and octahydrophenanthrenes can be mentioned, and specific examples thereof include tetralin, alkyl tetralin, indane, alkyl indane, octahydrophenanthrene, alkyl octahydrophenanthrene, octahydroanthracene, and alkyl octahydroanthracene, but among these, tetralin, alkyl tetralin, indane, and alkyl indane are particularly preferable.

Since these components are mixed in an actual light feedstock oil, the separate use of the respective components is not practical and a total amount of these components may be 10 mass % or higher. Examples of a method of analyzing a content ratio (mass %) of monocyclic naphthenobenzenes include a method based on a two-dimensional gas chromatographic method.

In the present invention, the reason why the content ratio of monocyclic naphthenobenzenes in the light feedstock oil is adjusted to be larger than the content ratio of monocyclic naphthenobenzenes in the feedstock oil is that monocyclic naphthenobenzenes can be effectively converted into monocyclic aromatic compounds having 6 to 8 carbon atoms when the monocyclic naphthenobenzenes are brought into contact with the catalyst of the present invention.

The content ratio of the monocyclic naphthenobenzenes is within the preferable range (10 to 70 mass %), as long as the light feedstock oil meets the predetermined distillation range.

The content ratio of hydrocarbons other than the monocyclic naphthenobenzenes is not particularly limited, and naphthenobenzenes other than monocyclic naphthenobenzenes, polycyclic aromatic hydrocarbons having two or more rings, saturated hydrocarbons such as paraffin, naphthene and the like, monocyclic aromatic hydrocarbons such as monocyclic alkyl benzenes, or the like may be included in the light feedstock oil.

However, when naphthenobenzenes other than monocyclic naphthenobenzenes, for example, the bicyclic naphthenobenzenes such as dihydrophenanthrene and tetrahydroanthracene are used, the cracking of the aromatic ring portion thereof hardly proceeds, and hence, the yield of monocyclic aromatic hydrocarbons cannot be improved. Therefore, the large amount of the bicyclic naphthenobenzenes is not always preferred. However, since the transition from the bicyclic naphthenobenzenes to the monocyclic aromatic hydrocarbons can be made by the hydrogen transfer reaction with the saturated hydrocarbons, the bicyclic naphthenobenzene can be contained in the light feedstock oil, as well as other polycyclic aromatic hydrocarbons.

Further, among polycyclic aromatic hydrocarbons, the tricyclic or higher-cyclic aromatic hydrocarbons exhibit low reactivity in a monocyclic aromatic hydrocarbon production process (sometimes referred to as a "cracking and reforming reaction process"), and therefore, the large amount of the tricyclic or higher-cyclic aromatic hydrocarbons is not preferred. Therefore, the amount of the tricyclic or higher-cyclic aromatic hydrocarbons in the feedstock oil is preferably 0.1 to 10 vol %, and more preferably 0.2 to 5 vol %, with respect to 100 mass % of the feedstock oil. Moreover, the tricyclic or higher-cyclic aromatic hydrocarbons may contains hetero atoms such as sulfur, oxygen, nitrogen and the like, within the range of not remarkably inhibiting the targeted reaction.

(Reaction Format)

Examples of the reaction format used when the light feedstock oil is brought into contact with a catalyst for monocyclic aromatic hydrocarbon production to react therewith, include a fixed bed, a mobile bed, and a fluidized bed. In the present invention, since heavy fraction are used as a feedstock, a fluidized bed which is capable of continuously removing the coke fraction adhering to the catalyst and is capable of stably carrying out the reaction is preferred. Further, a continuously regenerative type fluidized bed in which a catalyst is circulated between a reactor and a regenerator so that reaction-regeneration can be continuously repeated, is particularly preferred. When brought into contact with the catalyst, the light feedstock is preferably in a gas phase. Furthermore, the light feedstock may also be diluted with a gas as necessary.

(Catalyst for Monocyclic Aromatic Hydrocarbon Production)

[Crystalline Aluminosilicate]

From the viewpoint of further increasing the yield of monocyclic aromatic hydrocarbons, the crystalline aluminosilicate is preferably a zeolite with medium-sized pores and/or a zeolite with large-sized pores.

The zeolite with medium-sized pores is a zeolite having a 10-membered ring skeletal structure, and examples of the zeolite with medium-sized pores include zeolites having AEL type, EUO type, FER type, HEU type, MEL type, MFI type, NES type, TON type, and WEI type crystal structures. Among these, MFI type zeolite is preferable from the viewpoint that the yield of monocyclic aromatic hydrocarbons can be further increased.

The zeolite with large-sized pores is a zeolite having a 12-membered ring skeletal structure, and examples of the zeolite with large-sized pores include zeolites having AFI type, ATO type, BEA type, CON type, FAU type, GME type, LTL type, MOR type, MTW type, and OFF type crystal structures. Among these, from the viewpoint of industrial applicability, BEA type, FAU type and MOR type zeolites are preferable, and from the viewpoint that the yield of monocyclic aromatic hydrocarbons can be increased, BEA type zeolite is preferable.

The crystalline aluminosilicate may also contain a zeolite with small-sized pores, having a 10-membered or less-membered ring skeletal structure, and a zeolite with ultra-large-sized pores, having a 14-membered or more-membered ring skeletal structure, in addition to the zeolite with medium-sized pores and the zeolite with large-sized pores.

Here, examples of the zeolite with small-sized pores include zeolites having ANA type, CHA type, ERI type, GIS type, KFI type, LTA type, NAT type, PAU type and YUG type crystal structures.

Examples of the zeolite with ultra-large-sized pores include zeolites having CLO type and VPI type crystal structures.

In the case where a fixed bed reaction is applied to the cracking and reforming reaction process, the content of the crystalline aluminosilicate in the catalyst for monocyclic aromatic hydrocarbon production is preferably 60 mass % to 100 mass %, more preferably 70 mass % to 100 mass %, and particularly preferably 90 mass % to 100 mass %, when the total amount of the catalyst for monocyclic aromatic hydrocarbon production is designated as 100 mass %. When the content of the crystalline aluminosilicate is 60 mass % or more, the yield of monocyclic aromatic hydrocarbons can be sufficiently increased.

In the case where a fluidized bed reaction is applied to the cracking and reforming reaction process, the content of the crystalline aluminosilicate in the catalyst for monocyclic aromatic hydrocarbon production is preferably 20 mass % to 60 mass %, more preferably 30 mass % to 60 mass %, and particularly preferably 35 mass % to 60 mass %, when the total amount of the catalyst for monocyclic aromatic hydrocarbon production is designated as 100 mass %. When the content of the crystalline aluminosilicate is 20 mass % or more, the yield of monocyclic aromatic hydrocarbons can be sufficiently increased. When the content of the crystalline aluminosilicate is more than 60 mass %, the content of a binder that can be incorporated into the catalyst is decreased, and the catalyst may not be suitable for fluidized bed applications.

[Phosphorus and Boron]

The catalyst for monocyclic aromatic hydrocarbon production preferably contains phosphorus and/or boron. When the catalyst for monocyclic aromatic hydrocarbon production contains phosphorus and/or boron, a decrease in the yield of monocyclic aromatic hydrocarbons over time can be prevented, and coke production on the catalyst surface can be suppressed.

Examples of the method for incorporating phosphorus to the catalyst for monocyclic aromatic hydrocarbon production include a method of supporting phosphorus on a crystalline aluminosilicate, a crystalline aluminogallosilicate or a crystalline aluminozincosilicate, by an ion exchange method, an impregnation method or the like; a method of incorporating a phosphorus compound during zeolite synthesis and substituting a portion in the skeleton of a crystalline aluminosilicate with phosphorus; and a method of using a crystallization accelerator containing phosphorus during zeolite synthesis. The phosphate ion-containing aqueous solution used for incorporating phosphorous to the catalyst is not particularly limited, but solutions prepared by dissolving phosphoric acid, diammonium hydrogen phosphate, ammonium dihydrogen phosphate, and other water-soluble phosphates in water at arbitrary concentrations can be preferably used.

Examples of the method of incorporating boron into the catalyst for monocyclic aromatic hydrocarbon production include a method of supporting boron on a crystalline aluminosilicate, a crystalline aluminogallosilicate or a crystalline aluminozincosilicate, by an ion exchange method, an impregnation method or the like; a method of incorporating a boron compound during zeolite synthesis and substituting a portion of the skeleton of a crystalline aluminosilicate with boron; and a method of using a crystallization accelerator containing boron during zeolite synthesis.

The content of phosphorus and/or boron in the catalyst for monocyclic aromatic hydrocarbon production is preferably 0.1 mass % to 10 mass %, with respect to the total weight of the catalyst, and the lower limit is more preferably 0.5 mass % or more, while the upper limit is more preferably 9 mass % or less, and particularly preferably 8 mass % or less.

When the content of phosphorus with respect to the total weight of the catalyst is 0.1 mass % or more, a decrease in the yield of monocyclic aromatic hydrocarbons over time can be prevented, and when the content is 10 mass % or less, the yield of monocyclic aromatic hydrocarbons can be increased.

[Gallium and Zinc]

In the catalyst for monocyclic aromatic hydrocarbon production, gallium and/or zinc can be incorporated as necessary. When gallium and/or zinc is incorporated, the production proportion of monocyclic aromatic hydrocarbons can be further increased.

The form of gallium incorporation in the catalyst for monocyclic aromatic hydrocarbon production may be a form in which gallium is incorporated into the lattice skeleton of a crystalline aluminosilicate (crystalline aluminogallosilicate), a form in which gallium is supported on a crystalline aluminosilicate (gallium-supporting crystalline aluminosilicate), or both of the forms.

The form of zinc incorporation in the catalyst for monocyclic aromatic hydrocarbon production may be a form in which zinc is incorporated into the lattice skeleton of a crystalline aluminosilicate (crystalline aluminozincosilicate), a form in which zinc is supported on a crystalline aluminosilicate (zinc-supporting crystalline aluminosilicate), or both of the forms.

The crystalline aluminogallosilicate and crystalline aluminozincosilicate have a structure in which $SiO_4$, $AlO_4$ and $GaO_4/ZnO_4$ structures exist in the skeletal structure. Furthermore, the crystalline aluminogallosilicate and crystalline aluminozincosilicate are obtained by, for example, gel crystallization by hydrothermal synthesis, a method of inserting gallium or zinc into the lattice skeleton of a crystalline aluminosilicate, or a method of inserting aluminum into the lattice skeleton of a crystalline gallosilicate or a crystalline zincosilicate.

The gallium-supporting crystalline aluminosilicate is a compound in which gallium is supported on a crystalline aluminosilicate according to a known method such as an ion exchange method or an impregnation method. The gallium source used in these methods is not particularly limited, but examples thereof include gallium salts such as gallium nitrate and gallium chloride, and gallium oxide.

The zinc-supporting crystalline aluminosilicate is a compound in which zinc is supported on a crystalline aluminosilicate according to a known method such as an ion exchange method or an impregnation method. The zinc source used in these methods is not particularly limited, but examples thereof include zinc salts such as zinc nitrate and zinc chloride, and zinc oxide.

When the catalyst for monocyclic aromatic hydrocarbon production contains gallium and/or zinc, the content of gallium and/or zinc in the catalyst for monocyclic aromatic hydrocarbon production is preferably 0.01 mass % to 3.0 mass % with respect to 100 mass % of the total amount of the catalyst, and more preferably 0.05 mass')/0 to 1.5 mass %. When the content of gallium and/or zinc is 0.01 mass % or more, the production proportion of monocyclic aromatic hydrocarbons can be further increased. When the content is 3.0 mass % or less, dehydrogenation of naphthenobenzenes is suppressed and thus, monocyclic aromatic hydrocarbons can be produced more efficiently from the feedstock oil.

[Shape]

The catalyst for monocyclic aromatic hydrocarbon production is produced into, for example, a powder form, a granular form, a pellet form or the like according to the reaction format. For example, in the case of a fluidized bed, the catalyst is produced in a powder form, and in the case of a fixed bed, the catalyst is produced in a granular form or a pellet form. The average particle size of the catalyst used in a fluidized bed is preferably 30 μm to 180 μm, and more preferably 50 μm to 100 μm. Further, the bulk density of the catalyst used in a fluidized bed is preferably 0.4 g/cc to 1.8 g/cc, and more preferably 0.5 g/cc to 1.0 g/cc.

The average particle size represents the particle size of 50 mass % in a particle size distribution obtained by classification using sieves, and the bulk density is a value measured by the method of MS Standards R9301-2-3.

In the case of obtaining a granular or pellet-like catalyst, an oxide which is inert to the catalyst is incorporated as a binder as necessary, and then, the mixture may be molded by using various molding machines.

When the catalyst for monocyclic aromatic hydrocarbon production contains an inorganic oxide such as a binder, a catalyst containing phosphorus as a binder may also be used.

(Reaction Temperature)

The reaction temperature when bringing the feedstock oil into contact with the catalyst for monocyclic aromatic hydrocarbon production to react therewith is not particularly limited, but the reaction temperature is preferably 400° C. to 650° C. When the lower limit of the reaction temperature is 400° C. or higher, the reaction of the feedstock oil can be facilitated, and the lower limit is more preferably 450° C. or higher. When the upper limit of the reaction temperature is 650° C. or lower, the yield of monocyclic aromatic hydrocarbons can be sufficiently increased, and the upper limit is more preferably 600° C. or lower.

(Reaction Pressure)

The reaction pressure employed when the feedstock oil is brought into contact with the catalyst for monocyclic aromatic hydrocarbon production to react therewith is preferably set to 1.5 MPaG or less, and more preferably to 1.0 MPaG or less. When the reaction pressure is 1.5 MPaG or less, by-production of light gas can be suppressed, and also, pressure resistance of the reaction unit can be lowered. The lower limit of the reaction pressure is not particularly limited, but a normal pressure is preferable from the viewpoint of cost.

(Contact Time)

The contact time between the feedstock oil and the catalyst for monocyclic aromatic hydrocarbon production is not particularly limited so long as the desired reaction substantially proceeds. However, for example, the time for gas passage on the catalyst for monocyclic aromatic hydrocarbon production is preferably 1 second to 300 seconds, and the lower limit is more preferably 5 seconds or longer, while the upper limit is more preferably 150 seconds or shorter.

When the contact time is 1 second or longer, the reaction can be reliably achieved, and when the contact time is 300 seconds or shorter, deposition of carbon matter on the catalyst caused by coking or the like can be suppressed. Also, the amount of light gas generated by cracking can be suppressed.

According to the method of producing monocyclic aromatic hydrocarbons as described above, the content ratio of monocyclic naphthenobenzenes can be improved by using the light feedstock oil, and therefore, monocyclic aromatic hydrocarbons can be effectively produced.

EXAMPLES

Hereinafter, the invention will be more specifically described based on Examples and Comparative Examples, but the invention is not limited by these Examples.

[Preparation Example of Catalyst]

Preparation of Catalyst Containing Crystalline Aluminosilicate:

A solution (A) composed of 1706.1 g of sodium silicate (J sodium silicate No. 3, $SiO_2$: 28 mass % to 30 mass %, Na: 9 mass % to 10 mass %, balance water, manufactured by Nippon Chemical Industrial Co., Ltd.) and 2227.5 g of water, and a solution (B-1) composed of 64.2 g of $Al_2(SO_4)_3$.14 to $18H_2O$ (reagent grade, manufactured by Wako Pure Chemical Industries, Ltd.), 369.2 g of tetrapropylammonium bromide, 152.1 g of $H_2SO_4$ (97 mass %), 326.6 g of NaCl and 2975.7 g of water were each prepared.

Next, while the solution (A) was stirred at room temperature, the solution (B-1) was slowly added to the solution (A). The mixture thus obtained was vigorously stirred for 15 minutes in a mixer, and the gel was crushed to obtain a homogenously fine emulsified-state.

Subsequently, this mixture was placed in an autoclave made of stainless steel, and a crystallization operation was carried out under self-pressure under the conditions including a temperature of 165° C., a time of 72 hours, and a stirring speed of 100 rpm. After completion of the crystallization operation, the product was filtered to collect a solid product, and washing and filtration was repeated 5 times by using about 5 liters of deionized water. The solid obtained by filtration was dried at 120° C., and the solid was calcined at 550° C. for 3 hours under a stream of air.

It was confirmed by an X-ray diffraction analysis that the calcination product thus obtained had an MFI structure. Further, the $SiO_2/Al_2O_3$ ratio (molar ratio) obtained by a MASNMR analysis was 64.8. Furthermore, the content of the aluminum element contained in the lattice structure calculated from these results was 1.32 mass %.

Subsequently, a 30 mass % aqueous solution of ammonium nitrate was added at a ratio of 5 mL per 1 g of the calcination product thus obtained, and the mixture was heated and stirred at 100° C. for 2 hours, subsequently filtered and washed with water. This operation was repeated 4 times, and then the mixture was dried at 120° C. for 3 hours. Thus, an ammonium type crystalline aluminosilicate was obtained. Thereafter, calcination was carried out for 3 hours at 780° C., and thus a proton type crystalline aluminosilicate was obtained.

Subsequently, 120 g of the proton type crystalline aluminosilicate thus obtained was impregnated with 120 g of an aqueous solution of gallium nitrate such that 0.4 mass % (a value calculated with respect to 100 mass % of the total mass of the crystalline aluminosilicate) of gallium would be supported, and the resultant was dried at 120° C. Thereafter, the product was calcined at 780° C. for 3 hours under an air stream, and thus a gallium-supported crystalline aluminosilicate was obtained.

Subsequently, 30 g of the gallium-supported crystalline aluminosilicate thus obtained was impregnated with 30 g of an aqueous solution of diammonium hydrogen phosphate such that 0.7 mass % of phosphorus (a value calculated with respect to 100 mass % of the total mass of the crystalline aluminosilicate) would be supported, and the resultant was dried at 120° C. Thereafter, the product was calcined at 780° C. for 3 hours under an air stream, and thus a catalyst containing a crystalline aluminosilicate, gallium and phosphorus was obtained.

The crystalline aluminosilicate containing gallium and phosphorus thus obtained was tabletted by applying a pressure of 39.2 MPa (400 kgf), and the catalyst was coarsely crushed and adjusted to a 20 to 28 mesh size. Thus, a granular catalyst (hereinafter, also referred to as "granulated catalyst") was obtained.

Example 1

Example 1 Using Lightened Feedstock Oil (Preparation of Feedstock Oil)

A light cycle oil (LCO1) produced by a fluid catalytic cracking apparatus was prepared as a feedstock oil. The composition of the LCO1 was as follows: a total amount (saturated fraction+olefin fraction) of saturated fraction (total amount of paraffin fraction and naphthene fraction) and unsaturated fraction (olefin fraction): 22 mass, bicyclic naphthene fraction: 2 mass %, monocyclic naphthenobenzene fraction: 9 mass %, monocyclic aromatic fraction: 30 mass %, bicyclic aromatic fraction: 39 mass %, and tricyclic or higher-cyclic aromatic fraction: 9 mass %.

With respect to of the LCO1, the 10 vol % distillation temperature was 213° C., and the 90 vol % distillation temperature was 343° C.

The properties of the LCO 1 are shown in Table 1.

The LCO1 was subjected to fractional distillation by distillation, thereby obtaining light LCO1 having the 90 vol % distillation temperature of 295° C. The content ratio of monocyclic naphthenobenzenes in the obtained light LCO1 was 14 mass %. The properties of the light LCO 1 are shown in Table 1.

The compositions shown in Table 1 was analyzed by a method of using a two-dimensional gas chromatography apparatus (manufactured by ZOEX Corp., KT2006 GC×GC system,) and compositions of subsequent feedstock oils and light feedstock oils were analyzed in the same manner.

(Fixed Bed Reaction Test)

Using a flow type reaction apparatus of which a reactor was filled with 5.5 g of a granulated catalyst, the light LCO1 was brought into contact with the granulated catalyst to react therewith under the conditions including a reaction temperature of 540° C. and a reaction pressure of 0.3 MPaG. The contact time between the feedstock and the zeolite component contained in the granulated catalyst was set to 12 seconds.

When the feedstock are allowed to react for 30 minutes, and then a composition analysis of a product by gas chromatography directly connected to the apparatus was carried out, the yield of monocyclic aromatic hydrocarbons having 6 to 8 carbon atoms was 38 mass %, and the yield of cracked gas (hydrogen, methane, ethane, ethylene, LPG) was 15 mass %. The results are shown in Table 1.

Example 2

Example 2 Using Lightened Feedstock Oil

The LCO1 was subjected to fractional distillation by distillation, thereby obtaining light LCO2 having the 90 vol % distillation temperature of 271° C. The content ratio of monocyclic naphthenobenzenes in the obtained light LCO2 was 16 mass %. The properties of the light LCO2 are shown in Table 1.

The reaction test was conducted in the same condition as in Example 1, except that the light LCO2 was used instead of the light LCO1. As a result, the yield of monocyclic aromatic hydrocarbons having 6 to 8 carbon atoms was 43 mass %, the yield of cracked gas was 13 mass %. The results are shown in Table 1.

Example 3

Example 3 Using Lightened Feedstock Oil

The LCO1 was subjected to fractional distillation by distillation, thereby obtaining light LCO3 having the 90 vol % distillation temperature of 244° C. The content ratio of monocyclic naphthenobenzenes in the obtained light LCO3 was 18 mass %.

The reaction test was conducted in the same condition as in Example 1, except that the light LCO3 was used instead of the light LCO1. As a result, the yield of monocyclic aromatic hydrocarbons having 6 to 8 carbon atoms was 45 mass %, the yield of cracked gas was 13 mass %. The results are shown in Table 1.

Comparative Example 1

Example Using Feedstock Oil with Content Ratio of Monocyclic Naphthenobenzenes not Adjusted:

The reaction test was conducted in the same condition as in Example 1, except that the LCO1 was used instead of the light LCO1. As a result, the yield of monocyclic aromatic hydrocarbons having 6 to 8 carbon atoms was 32 mass %, the yield of cracked gas was 10 mass %. The results are shown in Table 1.

Example 4

Example 4 Using Lightened Feedstock Oil

A mixed solution containing 106 g of sodium silicate (J Sodium Silicate No. 3, $SiO_2$: 28 mass % to 30 mass %, Na: 9 mass % to 10 mass %, remainder: water, manufactured by Nippon Chemical Industrial Co., Ltd.) and pure water was added dropwise to a dilute sulfuric acid to prepare a silica sol aqueous solution ($SiO_2$ concentration: 10.2%). Meanwhile, distilled water was added to 20.4 g of the crystalline aluminosilicate, which had been prepared in the [Preparation Example of Catalyst], containing gallium and phosphorus to prepare a zeolite slurry. The zeolite slurry was mixed with 300 g of the silica sol aqueous solution, and the resulting slurry was spray dried at 250° C., obtaining a spherically shaped catalyst. Subsequently, the catalyst was calcined for 3 hours at 600° C., obtaining a powdered catalyst (hereinafter, referred to as the "powdered catalyst") having an average particle size of 84 μm and a bulk density of 0.74 g/cc.

(Fluidized Bed Reaction Test)

Using a fluidized bed reaction apparatus of which a reactor was filled with a powered catalyst (400 g), monocyclic aromatic hydrocarbons were produced under the conditions including a reaction temperature of 540° C., a reaction pressure of 0.3 MPaG, a contact time between the light LCO 1 and the zeolite component contained in the powered catalyst of 12 seconds. As a result, an amount of monocyclic aromatic hydrocarbons having 6 to 8 carbon atoms produced was 35 mass %, and an amount of cracked gas produced was 14 mass %. The results are shown in Table 1.

TABLE 1

| | | | Analysis method | Example 1 | Example 2 | Example 3 | Example 4 | Comparative Example 1 |
|---|---|---|---|---|---|---|---|---|
| | | | | Light LCO 1 | Light LCO 2 | Light LCO 3 | Light LCO 1 | LCO 1 |
| | Density at 15° C. (g/cm³) | | JIS K 2249 | 0.915 | 0.908 | 0.897 | 0.915 | 0.933 |
| | Dynamic viscosity at 30° C. (mm²/s) | | JIS K 2283 | 2.16 | 1.86 | 140 | 2.16 | 3.01 |
| Distillation properties | initial boiling point (° C.) | | JIS K 2254 | 160 | 160 | 160 | 160 | 160 |
| | 10 vol % distillation temperature (° C.) | | | 201 | 199 | 175 | 201 | 213 |
| | 50 vol % distillation temperature (° C.) | | | 246 | 237 | 221 | 246 | 262 |
| | 90 vol % distillation temperature (° C.) | | | 295 | 271 | 244 | 295 | 343 |
| | end point (° C.) | | | 310 | 283 | 251 | 310 | 373 |
| Composition analysis | Saturated fraction + unsaturated fraction (mass %) | | Gas chromatographic method | 18 | 16 | 14 | 18 | 22 |
| | | Bicyclic naphthene fraction (mass %) | | 1 | 1 | 1 | 1 | 2 |
| | Monocyclic aromatic fraction (mass %) | | | 42 | 51 | 64 | 42 | 30 |
| | | Monocyclic naphthene fraction (mass %) | | 14 | 16 | 18 | 14 | 9 |
| | Bicyclic aromatic fraction (mass %) | | | 40 | 33 | 21 | 40 | 39 |
| | Tricyclic or higher-cyclic aromatic fraction (mass %) | | | 10 | 0 | 0 | 0 | 9 |
| | Catalyst | | | Granulated Catalyst | Granulated Catalyst | Granulated Catalyst | Powdered Catalyst | Granulated Catalyst |
| yield | Monocyclic aromatic hydrocarbon having 6 to 8 carbon atoms (mass %) | | Gas chromatographic method | 38 | 43 | 45 | 35 | 32 |
| | Cracked gas (mass %) | | | 15 | 13 | 13 | 14 | 10 |

From the results shown in Table 1, it was confirmed that monocyclic aromatic hydrocarbons having 6 to 8 carbon atoms could be efficiently produced in Examples 1 to 4 in which the content ratio of monocyclic naphthenobenzenes in the feedstock had been adjusted to 10 mass % or higher by distillation of LCO1 to lighten, in comparison with Comparative Example 1 in which LCO1 (the content ratio of monocyclic naphthenobenzenes was 9 mass %) of which the content ratio of monocyclic naphthenobenzenes had not been adjusted, was used.

INDUSTRIAL APPLICABILITY

The method of producing monocyclic aromatic hydrocarbons according to the present invention is useful for production of monocyclic aromatic hydrocarbons which can be used as high-octane gasoline base stocks or petrochemical feedstocks and offer high added value.

The invention claimed is:

1. A method of producing monocyclic aromatic hydrocarbons comprising:
   distilling a feedstock oil having a 10 vol % distillation temperature of 140° C. or higher and a 90 vol % distillation temperature of 380° C. or lower to obtain a light feedstock oil having a 10 vol % distillation temperature of 140° C. to 205° C. and a 90 vol % distillation temperature of 300° C. or lower, wherein a content ratio of monocyclic naphthenobenzenes in the light feedstock oil is higher than a content ratio of monocyclic naphthenobenzenes in the feedstock,
   contacting the light feedstock oil with a catalyst for monocyclic aromatic hydrocarbon production containing phosphorus and/or boron and a crystalline aluminosilicate in the absence of hydrogen gas to obtain monocyclic aromatic hydrocarbons,
   wherein a content of the phosphorus and/or boron in the catalyst is 0.1 mass % to 10 mass % based on the total mass of the catalyst, and
   wherein the contacting of the light feedstock oil with the catalyst is performed at a reaction pressure of 1.5 MPaG or less.

2. The method of producing monocyclic aromatic hydrocarbons according to claim 1,
   wherein the content ratio of monocyclic naphthenobenzenes in the light feedstock oil is 10 mass % to 70 mass %.

3. The method of producing monocyclic aromatic hydrocarbons according to claim 2,
   wherein the feedstock oil contains a light cycle oil which is produced by a fluid catalytic cracking apparatus.

4. The method of producing monocyclic aromatic hydrocarbons according to claim 1,
   wherein the content ratio of monocyclic naphthenobenzenes in the light feedstock oil is 12 mass % to 70 mass %.

5. The method of producing monocyclic aromatic hydrocarbons according to claim 4,
   wherein the feedstock oil contains a light cycle oil which is produced by a fluid catalytic cracking apparatus.

6. The method of producing monocyclic aromatic hydrocarbons according to claim 1,
   wherein the feedstock oil contains a light cycle oil which is produced by a fluid catalytic cracking apparatus.

7. The method of producing monocyclic aromatic hydrocarbons according to claim 1, wherein the contact time between the light feedstock oil and the catalyst is 1 second to 300 seconds.

* * * * *